United States Patent
Minami

(10) Patent No.: US 10,927,188 B2
(45) Date of Patent: Feb. 23, 2021

(54) METHOD FOR PRODUCING SHORT-CHAIN PEPTIDE-IMMOBILIZED CARRIER, AND SHORT-CHAIN PEPTIDE-IMMOBILIZED CARRIER

(71) Applicant: FUJIFILM Corporation, Tokyo (JP)

(72) Inventor: Koichi Minami, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/782,121

(22) Filed: Oct. 12, 2017

(65) Prior Publication Data

US 2018/0037669 A1 Feb. 8, 2018

Related U.S. Application Data

(63) Continuation of application No. PCT/JP2016/060907, filed on Apr. 1, 2016.

(30) Foreign Application Priority Data

Apr. 13, 2015 (JP) .............................. JP2015-081768
Sep. 3, 2015 (JP) .............................. JP2015-173944

(51) Int. Cl.
C07K 17/10 (2006.01)
C07K 17/06 (2006.01)

(52) U.S. Cl.
CPC .............. *C07K 17/10* (2013.01); *C07K 17/06* (2013.01)

(58) Field of Classification Search
None
See application file for complete search history.

(56) References Cited

U.S. PATENT DOCUMENTS

| 5,817,527 | A | 10/1998 | Piran et al. | |
|---|---|---|---|---|
| 5,932,483 | A * | 8/1999 | Baumann | A61K 38/164 424/185.1 |
| 6,420,518 | B1 * | 7/2002 | Chen | C07K 14/65 530/317 |
| 10,450,344 | B2 * | 10/2019 | Minami | C07K 1/22 |
| 2004/0132149 | A1 | 7/2004 | Wessig et al. | |
| 2009/0068246 | A1 * | 3/2009 | Kinney | A61K 38/39 424/423 |
| 2010/0291665 | A1 | 11/2010 | Margraf et al. | |
| 2012/0238477 | A1 | 9/2012 | Albert et al. | |
| 2013/0046056 | A1 | 2/2013 | Spector et al. | |
| 2014/0079753 | A1 * | 3/2014 | Darby | C07K 14/685 424/423 |

FOREIGN PATENT DOCUMENTS

| CN | 101910202 A | 12/2010 |
|---|---|---|
| CN | 102671637 A | 9/2012 |
| CN | 102895960 A | 1/2013 |
| JP | 2000-500441 A | 1/2000 |
| JP | 2010-001238 A | 1/2010 |
| JP | 2010-122071 A | 6/2010 |
| JP | 2012-12334 A | 1/2012 |
| JP | 2014-149199 A | 8/2014 |
| RU | 2515197 C1 | 5/2014 |
| WO | 97/17375 A1 | 5/1997 |
| WO | 00/23478 A1 | 4/2000 |
| WO | 01/98458 A2 | 12/2001 |
| WO | 02/051872 A1 | 7/2002 |
| WO | 02/066984 A2 | 8/2002 |
| WO | 2011/103668 A1 | 9/2011 |
| WO | 2011/116028 A1 | 9/2011 |
| WO | 2011133894 A2 | 10/2011 |
| WO | 2015/005859 A1 | 1/2015 |
| WO | 2015/034056 A1 | 3/2015 |
| WO | 2016/052073 A1 | 4/2016 |
| WO | WO2015052073 | * 4/2016 |

OTHER PUBLICATIONS

Lang et al. "Spectroscopic evidence that monoclonal antibodies recognize the dominant conformation of medium-sized synthetic peptides", Journal of Immunological Methods, 1994, v.170, No. 1, p. 103-115, DOI: 10.1016/0022-1759(94)90250-X.*
Communication dated Sep. 28, 20018 issued by the Canadian Intellectual Property Office in counterpart application No. 2,982,430.
Notification of Reason for Refusal dated Dec. 1, 2018 from the Korean Intellectual Property Office in counterpart application No. 10-20017-7029097.
Emma Lang et al., "Spectroscopic evidence that monoclonal antibodies recognize the dominant conformation of medium-sized synthetic peptides", Journal of Immunological Methods, Elsevier Science Publishers, Amsterdam, NL, vol. 170, No. 1, Mar. 29, 1994, pp. 103-115, XP023656965.
Communication dated Dec. 11, 2017, from European Patent Office in counterpart application No. 16779934.5.
Notification of Reason for Refusal dated Dec. 1, 2018 from the Korean Intellectual Property Office in counterpart application No. 10-2017-7029097.
Communication dated May 14, 2018, from the Intellectual Property Office of Singapore in counterpart Application No. 11201708170V.
Communication dated Aug. 21, 2018 from the Japanese Patent Office in counterpart Application No. 2017-512265.
Communication dated Mar. 15, 2019 issued by the European Patent Office in counterpart European Application No. 16779934.5.
Communication dated Aug. 15, 20018 issued by the Russian Intellectual Property Office in counterpart application No. 2017134828/10.

(Continued)

*Primary Examiner* — Maury A Audet
(74) *Attorney, Agent, or Firm* — Sughrue Mion, PLLC

(57) ABSTRACT

Provided is a method for producing a short-chain peptide-immobilized carrier that maintains a secondary structure of a short-chain peptide, the method including a step of preparing an alcohol solution containing an alcohol solvent, and a short-chain peptide having a plurality of immobilizing functional groups, the short-chain peptide having a secondary structure induced in the alcohol solvent; and a step of bringing a carrier coupled with a spacer having a reactive group that reacts with the immobilizing functional group, into contact with the alcohol solution, and thereby immobilizing the short-chain peptide to the spacer.

17 Claims, No Drawings

Specification includes a Sequence Listing.

(56) References Cited

OTHER PUBLICATIONS

Andrew C. Braisted and James A. Wells, "Minimizing a binding domain from protein A", Proc. Natl. Acad. Sci. USA, vol. 93, pp. 5688-5692, Jun. 1996, Biochemistry.
International Search Report dated Jun. 14, 2016, in counterpart International Application No. PCT/JP2016/060907.
Written Opinion of the International Searching Authority dated Jun. 14, 2016, in counterpart International Application No. PCT/JP2016/060907.
International Preliminary Report on Patentability dated Oct. 17, 2017, in counterpart International Application No. PCT/JP2016/060907.
Communication dated Jul. 20, 2018, from the European Patent Office in counterpart European Application No. 16779934.5.
Communication dated Oct. 22, 2019, from the European Patent Office in counterpart European Application No. 19187299.3.
James S. Huston, et al., "Multisite association by recombinant proteins can enhance binding selectivity. Preferential removal of immune complexes from serum by immobilized truncated FB analogues of the B domain from staphylococcal protein A", Biophysical Journal, Apr. 1, 1992, vol. 62, No. 1, pp. 87-91 (5 pages total).
Communication dated Jul. 17, 2019 from the Intellectual Property Office of Singapore in application No. 11201708170V.
Communication dated Jul. 26, 2019 from the Canadian Patent Office in application No. 2982430.
Ito et al., "Materials for enhancing cell adhesion by immobilization of cell-adhesive peptide", Journal of Biomedical Materials Research, 1991, vol. 25, pp. 1325-1337 (total 13 pages).
Steffens et al., "High density binding of proteins and peptides to poly(D,L-lactide) grafted with polyacrylic acid", Biomaterials, 2002, vol. 23, pp. 3523-3531 (total 9 pages).
Communication dated Jun. 26, 2019 from Russian Patent Office in counterpart RU Application No. 2017134828/10.
Communication dated Jun. 11, 2020 from the State Intellectual Property Office of the P.R.C. in Application No. 201680021604.1.
Communication dated Feb. 27, 2020 from the European Patent Office in European Application No. 19187299.3.
Communication dated Oct. 28, 2020, from the European Patent Office in European Application No. 19187299.3.

* cited by examiner

METHOD FOR PRODUCING SHORT-CHAIN PEPTIDE-IMMOBILIZED CARRIER, AND SHORT-CHAIN PEPTIDE-IMMOBILIZED CARRIER

CROSS-REFERENCE TO RELATED APPLICATIONS

This application is a Continuation of PCT International Application No. PCT/JP2016/060907 filed on Apr. 1, 2016, which claims priority under 35 U.S.C. § 119(a) to Japanese Patent Application No. 2015-081768 filed on Apr. 13, 2015 and Japanese Patent Application No. 2015-173944 filed on Sep. 3, 2015. Each of the above applications is hereby expressly incorporated by reference, in its entirety, into the present application.

BACKGROUND OF THE INVENTION

1. Field of the Invention

The present invention relates to a method for producing a short-chain peptide-immobilized carrier, and a short-chain peptide-immobilized carrier.

2. Description of the Related Art

In recent years, development of antibody drugs has been in active progress. It is because antibody drugs that use the human immune function can be expected to have high efficacy, while having relatively fewer adverse drug reactions, and therefore, antibody drugs seem promising to take a central role in medicine in the future. Technologies that are indispensable in the development and practical use of antibody drugs are technologies for continuous and high-speed purification of antibodies in large quantities. A method that is currently most generally utilized for the purification of antibodies is an affinity chromatography method of using protein A as a ligand.

However, since protein A is produced using a genetic engineering method, there is a problem that the production process is complicated, and in a case where protein A itself is used as a ligand for affinity chromatography, this consequently leads to high production cost.

In regard to such a problem, investigations have been conducted on using a short-chain peptide having a length of approximately 50 residues or fewer, the peptide being based on the amino acid sequence of the portion of protein A that interacts with IgG (Immunoglobulin G) (for example, Braisted, A. C., et al., "Minimizing a binding domain from protein A", Proceedings of the National Academy of Sciences of the United States of America, the National Academy of Sciences of the USA, June 1996, Vol. 93, No. 12, p. 5688-5692).

Meanwhile, regarding a method of immobilizing a short-chain peptide on a carrier, for example, a method of forming a two-dimensional micro thin film on a substrate as described in JP2010-001238A may be mentioned. This method includes a step of preparing, as an organic molecular material for forming a thin film, an organic molecular material having at least a peptide chain, the peptide chain satisfying the following three conditions: (1) the peptide chain comprises 4 to 50 amino acid residues, (2) the peptide chain has at least hydrophilic amino acid residues and hydrophobic amino acid residues, and (3) the peptide chain can adsorb onto a substrate and has an amino acid sequence that can form a β-sheet structure when the peptide chain is adsorbed; a step of preparing a solution containing the organic molecular material at a concentration at which the peptide chain can maintain an α-helix structure or a random coil structure, and having the organic molecular material molecules individually disengaged and dispersed therein; and a step of supplying the solution onto the surface of a substrate, causing the organic molecular material in the solution to adsorb onto the substrate, and also providing, on the substrate, a monomolecular layer formed as a result of the peptide chains of the organic molecular material respectively forming a β-sheet when adsorbed on the substrate.

SUMMARY OF THE INVENTION

However, according to the investigation conducted by the inventors of the present invention, in the method described in JP2010-001238A, it was difficult to immobilize a short-chain peptide on a carrier while maintaining the secondary structure induced in the short-chain peptide in the solution. Since a secondary structure that has been intentionally induced and formed cannot be directly immobilized, a problem occurs as the secondary structure of the short-chain peptide is changed as a result of immobilization, and the binding capacity of an antigen-antibody reaction or the like that utilizes three-dimensional structures is deteriorated or lost. Also, the method needs forming a monomolecular layer and requires high cost, and the product obtained by the method is not durable for practical use.

Thus, it is an object of the present invention to provide a method for producing a short-chain peptide-immobilized carrier capable of maintaining a secondary structure of a short-chain peptide.

The inventors of the present invention repeatedly conducted thorough investigations in order to solve the problems described above, and as a result, the inventors found that a short-chain peptide can be immobilized on a carrier while maintaining a secondary structure of the peptide, by including a step of preparing an alcohol solution containing an alcohol solvent and a short-chain peptide having a plurality of immobilizing functional groups, the short-chain peptide having a secondary structure that is induced in the alcohol solvent; and a step of bringing a carrier coupled with a spacer having a reactive group that reacts with the immobilizing functional group, into contact with the alcohol solution, and thereby immobilizing the short-chain peptide to the spacer. Thus, the inventors completed the present invention. In the present invention, a short-chain peptide-immobilized carrier capable of an antigen-antibody reaction can be obtained, and a carrier having high binding properties can be obtained. Furthermore, since a spacer having a reactive group is utilized, forming a monomolecular layer is unnecessary, and cost reduction can be achieved.

That is, the present invention provides the following (1) to (9).

(1) A method for producing a short-chain peptide-immobilized carrier, the method including a step of preparing an alcohol solution containing an alcohol solvent and a short-chain peptide having a plurality of immobilizing functional groups, the short-chain peptide having a secondary structure that is induced in the alcohol solvent; and a step of bringing a carrier coupled with a spacer having a reactive group that reacts with the immobilizing functional group, into contact with the alcohol solution, and thereby immobilizing the short-chain peptide to the spacer.

(2) The method for producing a short-chain peptide-immobilized carrier according to (1), wherein the short-chain peptide has 34 residues or fewer.
(3) The method for producing a short-chain peptide-immobilized carrier according to (1) or (2), wherein the short-chain peptide is immobilized to the spacer by covalent bonding.
(4) The method for producing a short-chain peptide-immobilized carrier according to any one of (1) to (3) described above, wherein the spacer has a molecular weight of 10,000 or less.
(5) The method for producing a short-chain peptide-immobilized carrier according to any one of (1) to (4) described above, wherein the immobilizing functional group is at least one selected from the group consisting of a thiol group and amino group.
(6) The method for producing a short-chain peptide-immobilized carrier according to any one of (1) to (5) described above, wherein the immobilizing functional group is positioned at at least one terminal of the short-chain peptide.
(7) The method for producing a short-chain peptide-immobilized carrier according to any one of (1) to (5) described above, wherein the short-chain peptide has a partial structure containing a plurality of amino acid residues having an immobilizing functional group and containing at least one amino acid residue that does not have an immobilizing functional group, between amino acid residues having an immobilizing functional group.
(8) A short-chain peptide-immobilized carrier having a carrier; a spacer bonded onto the carrier; and a short-chain peptide disposed on the spacer and maintaining a secondary structure.
(9) The short-chain peptide-immobilized carrier according to (8) described above, wherein the carrier is bonded to the spacer by covalent bonding.

According to the present invention, there can be provided a method for producing a short-chain peptide-immobilized carrier capable of maintaining a secondary structure of a short-chain peptide even in a water-based solvent.

According to the present invention, there can also be provided a short-chain peptide-immobilized carrier having a secondary structure of the short-chain peptide maintained even in a water-based solvent.

DESCRIPTION OF THE PREFERRED EMBODIMENTS

The method for producing a short-chain peptide-immobilized carrier of the present invention (hereinafter, may be simply referred to as "production method of the present invention") will be explained.

[Method for Producing Short-Chain Peptide-Immobilized Carrier]

The method for producing a short-chain peptide-immobilized carrier of the present invention includes a step of preparing an alcohol solution containing an alcohol solvent and a short-chain peptide having a plurality of immobilizing functional groups, the short-chain peptide having a secondary structure that is induced in the alcohol solvent (hereinafter, referred to as "Step A"); and a step of bringing a carrier coupled with a spacer having a reactive group that reacts with the immobilizing functional group, into contact with the alcohol solution, and thereby immobilizing the short-chain peptide to the spacer (hereinafter, hereinafter, referred to as "Step B").

Description of Terms

First, the terms used in the present invention will be described.

1. Short-Chain Peptide (1) Definition of Short-Chain Peptide

The term "short-chain peptide" refers to a peptide having a number of amino acid residues of about 50 or less. However, in the case of a fusion peptide in which a plurality of domains is bonded, the "short-chain peptide" refers to a fusion peptide having a total number of amino acid residues of about 50 or less.

(2) Short-Chain Peptide of the Present Invention

The short-chain peptide used in the present invention (hereinafter, may be referred to as "short-chain peptide of the present invention") has a secondary structure induced in an alcohol solvent, and has a plurality of immobilizing functional groups.

The short-chain peptide of the present invention has a secondary structure induced in an alcohol solvent. Here, the "secondary structure" refers to a partial three-dimensional structure of the main chain of the short-chain peptide, and examples of the secondary structure include structures such as an α-helix, a β-sheet, a β-turn, a $3_{10}$ helix, a π-helix, and a $2.2_7$ ribbon. The phrase "(having) a secondary structure induced in an alcohol solvent" means that the percentage content of a secondary structure in an alcohol solvent is 1.5 times or more the percentage content of the secondary structure in a water-based solvent at 10° C. to 30° C. and at a pH close to neutrality ranging from 5 to 9, such as a HEPES (4-(2-hydroxyethyl)-1-piperazine ethanesulfonic acid) buffer solution, a Tris buffer solution, or a phosphate buffer solution. The percentage content of the secondary structure in an alcohol solvent is preferably 2 times or more, and more preferably 3 times or more, the percentage content of the secondary structure in a water-based solvent. Here, the percentage content of a secondary structure can be calculated by CD (circular dichroism). For example, the percentage content of a secondary structure is obtained by measuring a CD spectrum using a circular dichroism dispersion meter (J-820, manufactured by JASCO Corp.), and analyzing the secondary structure using a protein secondary structure analysis program (JWSSE-480, manufactured by JASCO Corp.) based on the CD spectrum thus obtained.

The number of amino acid residues of the short-chain peptide of the present invention is not particularly limited as long as the number is 50 or less. From the viewpoint of the solubility in an alcohol solvent, the number of amino acid residues of the short-chain peptide of the present invention is preferably 34 or less, more preferably 30 or less, even more preferably 25 or less, and still more preferably 20 or less. Furthermore, from the viewpoint of inducing a secondary structure, the number of amino acid residues of the short-chain peptide of the present invention is preferably 5 or more, more preferably 7 or more, and even more preferably 10 or more. The number of amino acid residues of the short-chain peptide of the present invention is preferably in the range of 5 to 50 residues, more preferably in the range of 5 to 34 residues, even more preferably in the range of 7 to 30 residues, still more preferably in the range of 7 to 25 residues, and even more preferably in the range of 10 to 20 residues.

According to the present invention, in a case in which a numerical value range is described using the symbol "~", the two ends of the numerical value range should be included in the numerical value range. For example, a value range of "5~50" includes "5" as the lower limit, and "50" as the upper limit.

The molecular weight of the short-chain peptide of the present invention is not particularly limited.

From the viewpoint of antigenicity, the molecular weight of the short-chain peptide of the present invention is, as the sum of the molecular weights of the amino acid residues, preferably 5,000 or less, more preferably 3,500 or less, and even more preferably 3,000 or less. From the viewpoint of inducing a secondary structure, the molecular weight of the short-chain peptide of the present invention is, as the sum of the molecular weights of the amino acid residues, preferably 500 or more, more preferably 600 or more, and even more preferably 800 or more. Furthermore, from the viewpoint of inducing a secondary structure without expressing antigenicity, the molecular weight of the short-chain peptide of the present invention is preferably 500 to 5,000, more preferably 600 to 3,500, and even more preferably 800 to 3,000.

The amino acid residues that constitute the short-chain peptide of the present invention may include only those amino acid residues derived from naturally occurring amino acids, and may also include amino acid residues derived from non-naturally occurring amino acids. Naturally occurring amino acids and non-naturally occurring amino acids will be described later.

A plurality of immobilizing functional groups of the short-chain peptide of the present invention (hereinafter, may be referred to as "immobilizing functional groups of the short-chain peptide of the present invention") is not particularly limited as long as the immobilizing functional groups have reactivity with the functional groups of the spacer.

Examples of an immobilizing functional group of the short-chain peptide of the present invention include an amino group (forming an amide bond), a carboxyl group, a hydroxyl group, and a thiol group. Here, reactivity means a property by which an immobilizing functional group of the short-chain peptide of the present invention reacts with a functional group of the spacer, and forms a covalent bond. The covalent bond is not particularly limited; however, it is preferable that a stable bond is formed. Examples of the covalent bond include a disulfide bond, a peptide bond (amide bond), a phosphodiester bond, a glycoside bond, a diazo bond, a thioether bond, an olefin bond, an epoxy bond, and a bond obtainable as a result of a click chemistry reaction. Among these covalent bonds, from the viewpoint of bonding stability, the covalent bond is preferably selected from a peptide bond, a thioether bond, an olefin bond, and a bond obtainable as a result of a click chemistry reaction.

Examples of the immobilizing functional group of the short-chain peptide of the present invention include a thiol group, an amino group, a carboxyl group, a hydroxyl group, a phosphoric acid ester group, an epoxy group, a glycidyl group, an azide group, and an alkynyl group. The immobilizing functional group of the short-chain peptide of the present invention is preferably at least one selected from the group consisting of a thiol group and an amino group.

Regarding the type of the immobilizing functional group of the short-chain peptide of the present invention, one kind of functional group may be used, or two or more kinds of groups may be used in combination.

The position of the amino acid residues having an immobilizing functional group in the short-chain peptide of the present invention is not particularly limited. For example, the short-chain peptide of the present invention may have a structure in which amino acid residues having an immobilizing functional group are disposed concentratedly on either the N-terminal side or the C-terminal side of the peptide chain of the short-chain peptide of the present invention, or may have a structure in which the amino acid residues having an immobilizing functional group are disposed dispersively on both the N-terminal side and the C-terminal side.

A non-limiting example of the short-chain peptide having a structure in which the immobilizing functional groups are disposed concentratedly on the N-terminal side may be "KKKEQQNAFY" (SEQ ID NO: 47), in which three lysine residues (K) are bonded to the N-terminus of the peptide having an amino acid sequence set forth in SEQ ID NO: 1. A non-limiting example of the short-chain peptide having a structure in which the immobilizing functional groups are disposed concentratedly on the C-terminal side may be "EQQNAFYKKK" (SEQ ID NO: 48), in which three lysine residues (K) are bonded to the C-terminal of the peptide having an amino acid sequence set forth in SEQ ID NO: 1. A non-limiting example of the short-chain peptide having a structure in which the immobilizing functional groups are disposed dispersively on both the N-terminal side and the C-terminal side may be "KKKEQQNAFYKKK" (SEQ ID NO: 49), in which three lysine residues (K) are bonded to the N-terminus as well as the C-terminus of the peptide having an amino acid sequence set forth in SEQ ID NO:1. In this case, the immobilizing functional groups are an ε-amino group in a side chain of a lysine residue, and the amino group of the N-terminus.

Furthermore, the short-chain peptide may have a partial structure containing at least one amino acid residue that does not have an immobilizing functional group, between amino acid residues having an immobilizing functional group.

A non-limiting example of the short-chain peptide having a partial structure containing at least one amino acid residue that does not have an immobilizing functional group, between amino acid residues having an immobilizing functional group, may be "KEQQNAFYKEQQNAFYK" (SEQ ID NO: 50) that employs a lysine residue (K) as an amino acid residue having an immobilizing functional group, and employs "EQQNAFY", which is a peptide having an amino acid sequence set forth in SEQ ID NO:1 as a partial structure containing at least one amino acid residue that does not have an immobilizing functional group. Here, the immobilizing functional groups are an ε-amino group in a side chain of a lysine residue, and the amino group of the N-terminus.

The short-chain peptide of the present invention is preferably a short-chain peptide having an antibody-binding property.

Here, the antibody-binding property refers to a property of binding to an antibody or an antibody derivative with a certain affinity. Binding to an antibody or an antibody derivative is preferably binding by an antigen-antibody reaction, and the site of binding is preferably a constant region (Fc region, CL region, or CH region) of an antibody or an antibody derivative.

The "antibody" refers to an immunoglobulin, or an analogue, a fragment, or a fusion body thereof. Here, an analogue refers to a protein or a protein conjugate, which is produced naturally or artificially and maintains the structure or function of an immunoglobulin at least partially. A fragment refers to a protein having a partial structure of an immunoglobulin, the protein being produced by an enzymatic treatment or a genetic engineering-based design. Furthermore, a fusion body refers to a protein produced by genetically fusing a functional part of a protein having biological activity, such as one of various cytokines or cytokine receptors, with the entirety or a portion of an immunoglobulin. The antibody is preferably a monoclonal antibody or a fusion body having the Fc region of an immunoglobulin, and a monoclonal antibody is more preferred. According to the present invention, the immunoglobulin may be any one of the five classes (isotypes) of IgG (Immunoglobulin G), IgM (Immunoglobulin M), IgA (Immunoglobulin A), IgD (Immunoglobulin D), and IgE (Immunoglobulin E); however, the immunoglobulin is preferably IgG or IgM, and more preferably IgG.

The "antibody derivative" refers to a chimeric antibody obtained by fusing a Fc region of a human immunoglobulin with a Fab region of a non-human mammal immunoglobulin; a chimeric antibody obtained by fusing several Fc regions of a human immunoglobulin with several Fv regions of a non-human mammal immunoglobulin; a humanized antibody obtained by fusing the portions remaining after excluding the CDR (complementarity-determining region) portion of a human immunoglobulin, with the CDR portion of a non-human mammal immunoglobulin; a chimeric antibody obtained by fusing a Fc region of a non-human mammal immunoglobulin with a Fab region of a human immunoglobulin; a chimeric antibody obtained by fusing several Fc regions of a non-human mammal immunoglobulin with several Fv regions of a human immunoglobulin; a non-human mammalized antibody obtained by fusing the portions remaining after excluding the CDR portion of a human immunoglobulin, with the CDR portion of a non-human mammal immunoglobulin; a chimeric antibody obtained by fusing a Fc region of a non-human mammal immunoglobulin with a Fab region of a non-human mammal immunoglobulin; a chimeric antibody obtained by fusing several Fc regions of a non-human mammal immunoglobulin with several Fv regions of a non-human mammal immunoglobulin; a non-human mammalized antibody obtained by fusing the portions remaining after excluding the CDR (complementarity-determining region) portion of a non-human mammal immunoglobulin, with the CDR portion of a non-human mammal immunoglobulin; and proteins obtained by subjecting these antibodies to chemical modifications, the proteins maintaining the Fc region.

It is preferable that the short-chain peptide of the present invention has a structure composed of an antibody-binding domain and a spacer-binding domain, or a structure further containing a linker connecting between the domains. Furthermore, the short-chain peptide of the present invention may also be a fusion peptide having a plurality of antibody-binding domains. By immobilizing the short-chain peptide of the present invention having an antibody-binding property while maintaining the secondary structure, an antibody-adsorbent, an antibody-retaining carrier and the like can be realized at low cost.

The domain and the spacer will be described later.

The amino acid sequence of the antibody-binding domain is not particularly limited as long as the antibody-binding domain has an antibody-binding property and can be bound to an antibody or an antibody derivative. The amino acid sequence of the antibody-binding domain is preferably selected from the group consisting of amino acid sequences having a sequence homology of 85% or higher with at least one of the amino acid sequences set forth in SEQ ID NO:1 to SEQ ID NO:38 described in Table 1, and the amino acid sequence is more preferably selected from the group consisting of amino acid sequences having a sequence homology of 87% or higher, even more preferably selected from the group consisting of amino acid sequences having a sequence homology of 90% or higher, still more preferably selected from the group consisting of amino acid sequences having a sequence homology of 95% or higher, and particularly preferably selected from the group consisting of amino acid sequences set forth in SEQ ID NO:1 to SEQ ID NO:38.

Here, the sequence homology of two amino acid sequences is determined as follows.

(a) Alignment of Two Amino Acid Sequences is Performed

Alignment is performed so as to obtain the highest alignment score, by assigning a match with a score of +1, assigning a mismatch with a score of −1, and assigning a gap with a score of −1.

(b) Sequence Homology is Calculated

The sequence homology is calculated by the following formula, based on the alignment thus obtained.

Sequence homology [%]=(Number of matching positions/number of all positions)×100[%]

The number of all positions is the length of the alignment, and the number of matching positions is the number of positions having matching kinds of amino acids.

Here, the determination of whether the types of amino acid residues match is made by checking whether the structures of the side chains of the amino acids that serve as the bases of the amino acid residues (amino acid side chains) are identical. Meanwhile, the structures of the side chains of the amino acids that are related as enantiomers are not identical.

(c) Calculation Example of Sequence Homology

For example, the following amino acid sequences are considered.

```
                                        (SEQ ID NO: 1)
        Sequence A: EQQNAFY (SEQ ID NO: 51)
        Sequence B: KEQQSAFY
```

Alignment of these sequences under the conditions described above gives the following results. Here, the sites where the kinds of amino acid (residues) match between the sequence A and the sequence B are assigned with homology strings "|" in order to make it easy to see. The symbol "-" is a gap.

```
    Sequence A    -EQQNAFY        (SEQ ID NO: 1)
                   || | | ||
    Sequence B    KEQQSAFY        (SEQ ID NO: 51)
```

The score of this alignment is: Match (+1)×6+Mismatch (−1)×1+Gap (−1)×1=4.

In this example, since the number of all positions is 8, and the number of match positions is 6, the sequence homology calculated by the above formula is 6/8×100=75.0%.

Examples of an amino acid sequence having a sequence homology of 85% or higher with the amino acid sequence set forth in SEQ ID NO:1 (EQQNAFY) include the amino acid sequence set forth in SEQ ID NO:4 (EGQNAFY), the amino acid sequence set forth in SEQ ID NO:7 (EQNAFY), and the amino acid sequence set forth in SEQ ID NO:10 (EQQSAFY).

Examples of an amino acid sequence having a sequence homology of 85% or higher with the amino acid sequence set forth in SEQ ID NO:2 (EQQNAFYEILH) include the amino acid sequence set forth in SEQ ID NO:4 (EQQNAFYEILHL) and the amino acid sequence set forth in SEQ ID NO:11 (EQQSAFYEILH).

Examples of an amino acid sequence having a sequence homology of 85% or higher with the amino acid sequence set forth in SEQ ID NO:3 (EQQNAFYEILHL) include the amino acid sequence set forth in SEQ ID NO:2 (EQQNAFYEILH).

Examples of an amino acid sequence having a sequence homology of 85% or higher with the amino acid sequence set forth in SEQ ID NO:4 (EGQNAFY) include the amino acid sequence set forth in SEQ ID NO:1 (EQQNAFY), the amino acid sequence set forth in SEQ ID NO:7 (EQNAFY), and the amino acid sequence set forth in SEQ ID NO:10 (EQQSAFY).

Examples of an amino acid sequence having a sequence homology of 85% or higher with the amino acid sequence set forth in SEQ ID NO:5 (EGQNAFYEILH) include the amino acid sequence set forth in SEQ ID NO: 3 (EQQNAFYEILH), and the amino acid sequence set forth in SEQ ID NO:11 (EQQSAFYEILH).

Examples of an amino acid sequence having a sequence homology of 85% or higher with the amino acid sequence set forth in SEQ ID NO:6 (EGQNAFYEILHL) include the amino acid sequence set forth in SEQ ID NO:3 (EQQNAFYEILHL).

Examples of an amino acid sequence having a sequence homology of 85% or higher with the amino acid sequence set forth in SEQ ID NO:7 (EQNAFY) include the amino acid sequence set forth in SEQ ID NO:1 (EQQNAFY) and the amino acid sequence set forth in SEQ ID NO:4 (EGQNAFY).

Examples of an amino acid sequence having a sequence homology of 85% or higher with the amino acid sequence set forth in SEQ ID NO:8 (EQNAFYEILH) include the amino acid sequence set forth in SEQ ID NO:2 (EQQNAFYEILH), the amino acid sequence set forth in SEQ ID NO:5 (EGQNAFYEILH), and the amino acid sequence set forth in SEQ ID NO:9 (EQNAFYEILHL).

Examples of an amino acid sequence having a sequence homology of 85% or higher with the amino acid sequence set forth in SEQ ID NO:9 (EQNAFYEILHL) include the amino acid sequence set forth in SEQ ID NO:3 (EQQNAFYEILHL), the amino acid sequence set forth in SEQ ID NO:6 (EGQNAFYEILHL), and the amino acid sequence set forth in SEQ ID NO:8 (EQNAFYEILH).

Examples of an amino acid sequence having a sequence homology of 85% or higher with the amino acid sequence set forth in SEQ ID NO:10 (EQQSAFY) include the amino acid sequence set forth in SEQ ID NO:1 (EQQNAFY), and the amino acid sequence set forth in SEQ ID NO:13 (DQQSAFY).

Examples of an amino acid sequence having a sequence homology of 85% or higher with the amino acid sequence set forth in SEQ ID NO:11 (EQQSAFYEILH) include the amino acid sequence set forth in SEQ ID NO:2 (EQQNAFYEILH), the amino acid sequence set forth in SEQ ID NO:12 (EQQSAFYEILHL), and the amino acid sequence set forth in SEQ ID NO:14 (DQQSAFYEILH).

Examples of an amino acid sequence having a sequence homology of 85% or higher with the amino acid sequence set forth in SEQ ID NO:12 (EQQSAFYEILHL) include the amino acid sequence set forth in SEQ ID NO:3 (EQQNAFYEILHL), the amino acid sequence set forth in SEQ ID NO:11 (EQQSAFYEILH), and the amino acid sequence set forth in SEQ ID NO:15 (DQQSAFYEILHL).

Examples of an amino acid sequence having a sequence homology of 85% or higher with the amino acid sequence set forth in SEQ ID NO:13 (DQQSAFY) include the amino acid sequence set forth in SEQ ID NO:10 (EQQSAFY).

TABLE 1

| Sequence No. | Amino acid sequence (N-terminus → C-terminus) | Number of amino acid residues |
| --- | --- | --- |
| 1 | EQQNAFY | 7 |
| 2 | EQQNAFYEILH | 11 |
| 3 | EQQNAFYEILHL | 12 |
| 4 | EGQNAFY | 7 |
| 5 | EGQNAFYEILH | 11 |
| 6 | EGQNAFYEILHL | 12 |
| 7 | EQNAFY | 6 |
| 8 | EQNAFYEILH | 10 |
| 9 | EQNAFYEILHL | 11 |
| 10 | EQQSAFY | 7 |
| 11 | EQQSAFYEILH | 11 |
| 12 | EQQSAFYEILHL | 12 |
| 13 | DQQSAFY | 7 |
| 14 | DQQSAFYEILH | 11 |
| 15 | DQQSAFYEILHL | 12 |
| 16 | EAQQSAFY | 8 |
| 17 | EAQQSAFYEILH | 12 |
| 18 | EAQQSAFYEILHL | 13 |
| 19 | EQSAFY | 6 |
| 20 | EQSAFYEILH | 10 |
| 21 | EQSAFYEILHL | 11 |
| 22 | EAQQNAFY | 8 |
| 23 | EAQQNAFYEILH | 12 |
| 24 | EAQQNAFYEILHL | 13 |
| 25 | DAQQSAFY | 8 |
| 26 | DAQQSAFYEILH | 12 |
| 27 | DAQQSAFYEILHL | 13 |
| 28 | DQSAFY | 6 |
| 29 | DQSAFYEILH | 10 |
| 30 | DQSAFYEILHL | 11 |
| 31 | EQQKFY | 7 |
| 32 | EQQNKFY | 7 |
| 33 | EQQSKFY | 7 |
| 34 | EQQKAFY | 7 |
| 35 | EAQQKKFY | 8 |
| 36 | EAQQNKFY | 8 |

TABLE 1-continued

| Sequence No. | Amino acid sequence (N-terminus → C-terminus) | Number of amino acid residues |
|---|---|---|
| 37 | EAQQSKFY | 8 |
| 38 | EAQQKAFY | 8 |

(3) Amino Acid Residue/Amino Acid 3.1) Amino Acid Residue

The term "amino acid residue" is as defined in the IUPAC (International Union of Pure and Applied Chemistry) Gold Book. That is, on the occasion in which two or more amino acids form a peptide by being bonded by peptide bonding between the molecules, the portion remaining after dehydration of an amino acid molecule at the time of forming peptide bonds is called an amino acid residue. Therefore, the unit that constitutes a peptide chain is an amino acid residue. Furthermore, in a peptide chain, the amino acid residue at the C-terminus is referred to as C-terminal residue, and the amino acid residue at the N-terminus is referred to as N-terminal residue. Amino acid residues are considered as amino acid residues of the same kind, if the amino acids from which the amino acid residues are derived are of the same kind.

3.2) Amino Acid

The term "amino acid" refers to, unless particularly stated otherwise, an organic compound having an amino group (—NH$_2$) or an imino group and a carboxyl group in the molecule, the organic compound being capable of forming a peptide when two or more thereof are bonded by peptide bonding.

The names and codes for amino acids will be indicated using, in principle, the names and codes adopted by the INTERNATIONAL UNION OF PURE AND APPLIED CHEMISTRY and INTERNATIONAL UNION OF BIOCHEMISTRY AND MOLECULAR BIOLOGY IUPAC-IUB Joint Commission on Biochemical Nomenclature (JCBN). Table 2 shows the names and codes (one letter codes and three letter codes) of α-amino acids whose one letter codes and three letter codes have been officially recognized. Meanwhile, the code "Xaa", which represents an arbitrary amino acid, can also be used in the case of indicating an amino acid other than the amino acids listed in Table 2.

TABLE 2

| Amino acid | One letter code | Three letter code |
|---|---|---|
| Alanine | A | Ala |
| Cysteine | C | Cys |
| Aspartic acid | D | Asp |
| Glutamic acid | E | Glu |
| Phenylalanine | F | Phe |
| Glycine | G | Gly |
| Histidine | H | His |
| Isoleucine | I | Ile |
| Lysine | K | Lys |
| Leucine | L | Leu |
| Methionine | M | Met |
| Asparagine | N | Asn |
| Pyrrolysine | O | Pyl |
| Proline | P | Pro |
| Glutamine | Q | Gln |

TABLE 2-continued

| Amino acid | One letter code | Three letter code |
|---|---|---|
| Arginine | R | Arg |
| Serine | S | Ser |
| Threonine | T | Thr |
| Selenocysteine | U | Sec |
| Valine | V | Val |
| Tryptophan | W | Trp |
| Tyrosine | Y | Tyr |
| Asp or Asn | B | Asx |
| Glu or Gln | Z | Glx |
| Arbitrary amino acid | X | Xaa |

According to the present invention, not only the amino acid residues derived from naturally occurring amino acids, but the amino acid residues derived from non-naturally occurring amino acids can also be used as the units that constitute a peptide chain. The short-chain peptide of the present invention may be composed of naturally occurring amino acids only, may be composed of non-naturally occurring amino acids only, or may include both naturally occurring amino acids and non-naturally occurring amino acids. The proportions (molar proportions) of naturally occurring amino acids and non-naturally occurring amino acids in a case in which the naturally occurring amino acids and the non-naturally occurring amino acids are included, are not particularly limited.

3.2.1) Naturally Occurring Amino Acids

The term "naturally occurring amino acid" refers to an amino acid encoded by the mRNA (messenger RNA; RNA=ribonucleotide) in nature. Naturally occurring amino acids specifically refer to 22 kinds of amino acids, including glycine (Gly), L-alanine (Ala), L-arginine (Arg), L-asparagine (Asn), L-aspartic acid (Asp), L-cysteine (Cys), L-glutamine (Gln), L-glutamic acid (Glu), L-histidine (His), L-isoleucine (Ile), L-leucine (Leu), L-lysine (Lys), L-methionine (Met), L-phenylalanine (Phe), L-proline (Pro), L-serine (Ser), L-threonine (Thr), L-tryptophan (Trp), L-tyrosine (Tyr), L-valine (Val), L-pyrrolysine (Pyl), and L-selenocysteine (Sec).

Enantiomers of these amino acids (except for glycine) are not included in the naturally occurring amino acids.

3.2.2) Non-Naturally Occurring Amino Acids

The term "non-naturally occurring amino acid" refers to an amino acid that is not encoded by the mRNA (messenger RNA; RNA=ribonucleotide) in nature. Examples of the non-naturally occurring amino acid include, but are not particularly limited to, enantiomers of naturally occurring amino acids (except for glycine), such as D-alanine (D-Ala), D-arginine (D-Arg), D-asparagine (D-Asn), D-aspartic acid (D-Asp), D-cysteine (D-Cys), D-glutamine (D-Gln), D-glutamic acid (D-Glu), D-histidine (D-His), D-isoleucine (D-Ile), D-leucine (D-Leu), D-lysine (D-Lys), D-methionine (D-Met), D-phenylalanine (D-Phe), D-proline (D-Pro), D-serine (D-Ser), D-threonine (D-Thr), D-tryptophan (D-Trp), D-tyrosine (D-Tyr), D-valine (D-Val), D-pyrrolysine (D-Pyl), and D-selenocysteine (D-Sec); non-naturally occurring α-amino acids such as 2-aminoadipic acid (Aad), 2-aminobutyric acid (Abu), 2-aminoheptanoic acid (Ahe), 2-aminoisobutyric acid (Aib), 2-aminopimelic acid (Apm), 2,4-diaminobutyric acid (Dbu), 2,2'-diaminopimelic acid (Dpm), 2,3-diaminopropionic acid (Dpr), allohydroxylysine (aHyl), alloisoleucine (aIle), norvaline (Nva), norleucine (Nle), ornithine (Orn), desmosine (Des), and isodesmosine (Ide); 6-N-methyllysine (MeLys), 3-hydroxyproline (3Hyp), 4-hydroxyproline (4Hyp), β-alanine (bAla), 3-aminoisobutyric acid (bAib), 3-aminoadipic acid (bAad), 4-aminobutyric acid (4Abu), and 6-aminocaproic acid (Acp).

The symbols described within parentheses after the names of the various non-naturally occurring amino acids are examples of the codes respectively representing the non-naturally occurring amino acids.

(4) Peptide/Fusion Peptide 4.1) Peptide

The term "peptide" is as defined in the International Union of Pure and Applied Chemistry (IUPAC) Gold Book. That is, a peptide is an amide compound obtainable as a result of two or more amino acids forming peptide bonds between the molecules.

Unless particularly specified, the amino acid sequence of a peptide (also referred to as "primary structure") is described by one-dimensionally arranging the amino acid residues such that the amino acid sequence has the N-terminus and the C-terminus arranged from the left-hand side end to the right-hand side end.

According to the present invention, the N-terminal amino group and the C-terminal carboxyl group of the peptide chain may be modified. Examples of the modification for the N-terminal amino group include acetylation and tert-butoxycarbonylation (Boc), and examples of the modification for the C-terminal carboxyl group include amidation and esterification.

4.2) Fusion Peptide

The term "fusion peptide" refers to a polymer compound constructed by linking two or more units of a peptide having some kind of physicochemical or biochemical function (corresponding to "domain") directly or via a linker.

The linker is not particularly limited as long as the linker is capable of linking between the domains. Examples of the linker include a peptide linker formed from a peptide chain, a PEG (polyethylene glycol) linker formed from a polyethylene glycol chain, a disulfide bond (SS bond), a thioether bond, an olefin bond, a bond obtainable as a result of a click chemistry reaction, and combinations of two or more of these.

4.2.1) Domain

The term "domain" refers to a part or region composed of one or more, preferably two or more, more preferably three or more, and even more preferably four or more, and several hundred or fewer amino acid residues that can express some kind of physicochemical or biochemical function (hereinafter, may be simply referred to as "function") of a protein (including a fusion protein) or a peptide (including a fusion peptide).

Domains can be classified into, for example, antibody-binding domains and spacer-binding domains, depending on the function.

4.2.1.1) Antibody-Binding Domain

Antibody-binding domains are domains composed of peptides a having antibody-binding property.

The antibody-binding property is as described above.

4.2.1.2) Spacer-Binding Domain

A spacer-binding domain is a part other than the antibody-binding domain, and is a domain containing an amino acid residue having an immobilizing functional group that binds to a spacer.

Regarding the spacer-binding domain, it is preferable that the spacer-binding domain includes one or more, preferably two or more, more preferably three or more, even more preferably three or more, and still more preferably four or more, amino acid residues each having one or more immobilizing functional groups at least in a side chain, per domain. Here, examples of the amino acid residue having an immobilizing functional group include an amino acid residue having an amino group in a side chain, such as a lysine residue (K), an ornithine residue, a diaminobutyric acid residue, a diaminopropionic acid residue, or a homolysine residue; an amino acid residue having a thiol group in a side chain, such as a cysteine residue (C) or a homocysteine residue; and an amino acid residue having a hydroxyl group in a side chain, such as serine (S), threonine (T), or tyrosine (Y). As a result of a coupling reaction between any one of these immobilizing functional groups and a functional group of a spacer, the short-chain peptide as a ligand is bonded to the spacer. In a case in which the functional group of the spacer is a carboxyl group, a lysine residue (K), an ornithine residue, a diaminobutyric acid residue, a homolysine residue, or a diaminopropionic acid residue, all of which have an amino group having reactivity with a carboxyl group, is preferred, and a lysine residue (K) is particularly preferred from the viewpoint of economic efficiency.

Furthermore, the short-chain peptide of the present invention may contain a plurality of spacer-binding domains.

4.2.2) Linker

The "linker" is a molecular chain or a bond mutually connecting domains in a fusion peptide.

Examples of the molecular chain include a peptide linker formed from an amino acid or a peptide, and a PEG (polyethylene glycol) linker formed from ethylene glycol or polyethylene glycol. Two or more kinds of linkers may be used in combination, and a linker may also include, for example, a peptide and PEG together.

Examples of the bond include a disulfide bond (SS bond), a thioether bond, an olefin bond, and a bond obtainable as a result of a click chemistry reaction.

The number of amino acid residues that constitute the peptide linker is not particularly limited as long as the number is 1 or larger; however, the number of amino acid residues is preferably 1 to 20, more preferably 1 to 10, and even more preferably 1 to 5.

Furthermore, the number of ethylene glycol units that constitute the PEG linker is not particularly limited as long as the number is 1 or larger; however, the number of amino acid residues is preferably 1 to 24, more preferably 1 to 12, and even more preferably 4 to 8.

Here, the type of the amino acid residues that can be included in the linker is not particularly limited; however, examples include Gly, Ala, and Ser, which have interactions with IgG antibodies to a less extent. The linker may also include an amino acid residue having an immobilizing functional group.

2. Alcohol Solvent

The alcohol solvent used in the present invention (may be simply referred to as "alcohol solvent of the present invention") is not particularly limited as long as it is a solvent including alcohol.

Examples of the alcohol include methanol, ethanol, 2-propanol (IPA, isopropyl alcohol), tert-butyl alcohol (tert-BuOH), 2,2,2-trifluoroethanol (TFE), and 1,1,1,3,3,3-hexafluoro-2-propanol (HFIP, hexafluoroisopropyl alcohol).

From the viewpoint of peptide solubility, the alcohol is preferably at least one selected from the group consisting of methanol, ethanol, and IPA.

The alcohols mentioned above can be used singly or in combination of two or more kinds thereof.

The alcohol solvent used at the time of inducing a secondary structure of a short-chain peptide and the alcohol solvent used at the time of immobilizing a short-chain peptide to a carrier, may be alcohol solvents of the same kind, or may be alcohol solvents of different kinds. For example, a short-chain peptide may be bonded to a spacer by immersing the short-chain peptide in methanol for a short time period to induce a secondary structure of the short-chain peptide, causing the short-chain peptide to adsorb onto a carrier, and immersing the short-chain peptide in isopropyl alcohol for a long time period.

The alcohol content in the alcohol solvent of the present invention is not particularly limited; however, from the viewpoint of forming a secondary structure, the alcohol content is preferably 20% (v/v) or more, more preferably 50% (v/v) or more, even more preferably 70% (v/v) or more, and still more preferably 95% (v/v) or more.

The solvent other than an alcohol in the alcohol solvent of the present invention is not particularly limited as long as it is a solvent that does not inhibit the formation of a secondary structure. The solvent other than an alcohol is preferably at least one selected from pure water and a buffer solution, and more preferably pure water, from the viewpoint of the peptide solubility. Examples of the buffer solution include a HEPES (4-(2-hydroxyethyl)-1-piperazine ethanesulfonic acid) buffer solution, a Tris (tris(hydroxymethyl)aminomethane) buffer solution, and a phosphate buffer solution.

3. Ligand/Antibody-Bindable Ligand

A "ligand" refers to a molecule that binds to a particular substance with a certain affinity. Such a molecule may be a protein, a peptide, a low-molecular weight compound, or the like.

An "antibody-bindable ligand" refers to a ligand having an antibody-binding property, that is, a ligand that binds to an antibody or an antibody derivative with a certain affinity. It is preferable that an antibody-bindable ligand binds to an antibody or an antibody derivative through an antigen-antibody reaction in which specific intermolecular affinity works. The site of the antibody or antibody derivative to which the antibody-bindable ligand binds is preferably a constant region (Fc region, CL region (constant region of a light chain), or CH region (constant region of a heavy chain)).

The ligand used in the present invention (hereinafter, may be simply referred to as "ligand of the present invention") is the short-chain peptide of the present invention as described above. As the ligand of the present invention, it is preferable to use a short-chain peptide having an antibody-binding property, among the short-chain peptides of the present invention.

4. Spacer

A "spacer" is a compound that is interposed between a carrier and a ligand.

The spacer used in the present invention (hereinafter, may be simply referred to as "spacer of the present invention") is a spacer having a reactive group that reacts with an immobilizing functional group carried by the short-chain peptide of the present invention, and it is preferable that the spacer has a functional group that forms a covalent bond with the short-chain peptide of the present invention.

Examples of the functional group include a thiol group, an amino group, a carboxyl group, a diazo group, a chloroacetyl group, an olefin group, a glycidyl group, a carbene group, a hydroxyl group, and a formyl group. From the viewpoint of binding stability, the functional group is preferably at least one selected from the group consisting of a thiol group, an amino group, a carboxyl group, a chloroacetyl group, and a glycidyl group, and more preferably at least one selected from the group consisting of a carboxyl group and a glycidyl group.

The spacer of the present invention is preferably a polyfunctional carboxylic acid, and particularly preferably polyacrylic acid. The polyacrylic acid may have a functional group such as an amino group added to the terminals.

The length of the spacer of the present invention is not particularly limited; however, it is preferable that the length is longer than the apparent length of the short-chain peptide having a secondary structure induced therein, so that the spacer can be covalently bonded to multiple points at positions including a site at which the secondary structure of the short-chain peptide changes in an alcohol solvent.

The molecular weight of the spacer of the present invention is not particularly limited. The molecular weight of the spacer of the present invention is, as the mass average molecular weight, preferably 10,000 or less, more preferably 9,000 or less, even more preferably 5,000 or less, and still more preferably 3,000 or less.

Furthermore, the molecular weight of the spacer of the present invention is, as the mass average molecular weight, preferably 300 or more, more preferably 500 or more, even more preferably 900 or more, and still more preferably 1,500 or more. The molecular weight of the spacer of the present invention is, as the mass average molecular weight, preferably in the range of 300 to 10,000, more preferably in the range of 900 to 9,000, even more preferably in the range of 900 to 5,000, and still more preferably in the range of 1,500 to 3,000.

If the molecular weight of the spacer of the present invention is too small, the number of spots of bonding to the short-chain peptide is small, and it is difficult to maintain a secondary structure of the short-chain peptide. If the molecular weight of the spacer of the present invention is too large, it is difficult to bond a large amount of the spacer of the present invention to a carrier.

The spacer is bonded to the carrier that will be described later, and it is preferable that the spacer is bonded directly to a functional group on the carrier, or bonded between functional groups on the carrier, through a covalent bond such as an amide bond, a maleimide bond, an ester bond, an ether bond, an epoxy bond, or an olefin bond. An amide bond or an epoxy bond, both of which have high binding power, is more preferred.

5. Carrier

A carrier is a base material that supports a ligand.

The carrier used in the present invention is preferably a water-insoluble carrier.

Examples of the water-insoluble carrier include polysaccharides such as crystalline cellulose, crosslinked cellulose, crosslinked agarose, crosslinked dextran, and crosslinked pullulan; organic carriers such as an acrylate-based polymer and a styrene-based polymer; inorganic carriers such as glass beads and silica gel; and organic-organic and organic-inorganic composite carriers obtainable by combinations thereof.

The water-insoluble carrier is more preferably a polysaccharide or an acrylate-based polymer, and even more preferably a polysaccharide such as agarose or cellulose, from the viewpoint of alkali resistance.

Examples of commercially available products that can be used as water-insoluble carriers include CELLUFINE GCL2000 (manufactured by JNC Corporation) and CELLUFINE MAX CM (manufactured by JNC Corporation), which are porous cellulose gels; SEPHACRYL S-1000 SF (manufactured by GE Healthcare, Inc.), which is obtained by crosslinking allyl dextran and methylenebisacrylamide by covalent bonding; TOYOPEARL (manufactured by Tosoh Corporation), TOYOPEARL AF-Carboxy-650 (manufactured by Tosoh Corporation), and TOYOPEARL GigaCap CM-650 (manufactured by Tosoh Corporation), all of which are acrylate-based carriers; SEPHAROSE CL4B (manufactured by GE Healthcare, Inc.), which is an agarose-based crosslinked carrier; EUPERGIT C250L (manufactured by Sigma-Aldrich Company), which is a polymethacrylamide activated with an epoxy group; and CM5 (manufactured by GE Healthcare, Inc.), which is a sensor chip coated with carboxymethyl dextran on the surface of a gold film. However, the water-insoluble carrier according to the present invention is not limited only to these carriers or activated carriers. Furthermore, the water-insoluble carrier used in the present invention is preferably a carrier having a large surface area in view of the purpose of use and method of this adsorbent material, and the water-insoluble carrier is preferably porous with a large number of pores having an appropriate size. The form of the carrier is not particularly limited; however, carriers in a bead form, a fiber form, a film form, and a hollow fiber form can all be used, and any arbitrary form can be selected.

<Step A/Step B>

The procedures of Step A and Step B will be explained.

1. Procedure of Step A

In Step A, the procedure of preparing an alcohol solution containing the short-chain peptide described above is not particularly limited, and for example, a method of adding a predetermined short-chain peptide to an alcohol solution, and leaving the mixture to stand for a predetermined time period may be used.

The concentration of the short-chain peptide in the alcohol solution is not particularly limited and may vary depending on the type of the short-chain peptide used; however, the concentration is preferably 0.0000001% to 5% by mass, more preferably 0.00001% to 1% by mass, and even more preferably 0.001% to 1% by mass, with respect to the total mass of the alcohol solution.

The pH of the alcohol solution is not particularly limited; however, it is preferable that the alcohol solution is adjusted within the range of pH 4 to 12.

The temperature employed at the time of preparing the alcohol solution is not particularly limited; however, it is preferable that the preparation is carried out at 2° C. to 50° C.

2. Procedure of Step B

In Step B, the method of bringing the above-mentioned carrier coupled with a spacer contact with the alcohol solution is not particularly limited, and for example, a method of adding the carrier coupled with a spacer to the alcohol solution may be used.

On the occasion of bringing the carrier coupled with a spacer into contact with the alcohol solution, if necessary, a compound that accelerates the reaction between an immobilizing functional group in the short-chain peptide and a reactive group in the spacer may be incorporated into the system. For example, in a case in which the reaction between the immobilizing functional group and the reactive group is a dehydration condensation reaction, it is preferable to use a so-called dehydration condensing agent (for example, (1-ethyl-3-(3-dimethylaminopropyl)carbodiimide)) or the like as the compound. In a case in which such a dehydration condensing agent is used, the dehydration condensing agent may be first brought into contact with a carrier coupled with a spacer, and then the system may be brought into contact with an alcohol solution. Furthermore, for example, in the case of disulfide bonding, it is preferable to use an oxidizing agent such as hydrogen peroxide or iodine. For example, in the case of glycoside bonding, it is preferable to incorporate an acid. In regard to the reaction between an immobilizing functional group in the short-chain peptide and a reactive group in the spacer, it is preferable to form an amide bond between an amino group and a carboxyl group by means of an amino coupling reaction. Furthermore, if necessary, at least one base selected from the group consisting of diazabicycloundecene (DBU), diazabicyclooctane (DABCO), diazabicyclononene (DBN), methylimidazole, dimethylaniline, triethylamine, and pyridine may also be added thereto.

The density of the short-chain peptide to be immobilized on the carrier is not particularly limited; however, the density is preferably 0.1 mmol to 1,000 mmol/1 L of the filler, more preferably 0.1 mmol to 500 mmol/1 L of the filler, and even more preferably 1 mmol to 100 mmol/1 L of the filler. In a case in which the density is in this range, a good balance is achieved between the amount of use of the short-chain peptide and the antibody purification performance, and antibodies can be purified efficiently at lower cost.

[Short-Chain Peptide-Immobilized Carrier]

A short-chain peptide-immobilized carrier having a carrier; a spacer bonded onto the carrier; and a short-chain peptide disposed on the spacer and maintaining a secondary structure, can be produced by the production method of the present invention.

When a short-chain peptide having an antibody-binding property is used as the short-chain peptide, the short-chain peptide-immobilized carrier of the present invention can be utilized as a carrier for affinity chromatography having excellent antibody-binding property. Furthermore, the short-chain peptide-immobilized carrier of the present invention is a carrier for affinity chromatography that is advantageous compared to protein A, in view of antigenicity and cost.

Hereinafter, the present invention will be described in more detail based on Examples; however, the present invention is not intended to be limited to these Examples.

EXAMPLES

[Synthesis of Peptide]

The short-chain peptides indicated in Table 3 were synthesized using a fully automated peptide synthesis apparatus (PSSM-8, manufactured by Shimadzu Corporation).

TABLE 3

| Short-chain peptide name | Sequence No. | Amino acid sequence (N-terminus → C-terminus) | Number of amino acid residues | Number of immobilizing functional groups |
| --- | --- | --- | --- | --- |
| Short-chain peptide 1 | 39 | KKKKKEQQNAFYEILHLPNLTEEQRNAFIQSLRD | 34 | 6 |
| Short-chain peptide 2 | 40 | KKKKKEQQNAFYEILH | 16 | 6 |

TABLE 3-continued

| Short-chain peptide name | Sequence No. | Amino acid sequence (N-terminus → C-terminus) | Number of amino acid residues | Number of immobilizing functional groups |
|---|---|---|---|---|
| Short-chain peptide 3 | 41 | KKKEQQNAFYEILHKKK | 17 | 7 |
| Short-chain peptide 4 | 42 | KKKKEQQNAFYEILHKKKK | 19 | 9 |
| Short-chain peptide 5 | 43 | Ac-KAAKEQQKAFYKILH[*1] | 15 | 4 |
| Short-chain peptide 6 | 44 | KKRREQQNAFYEILHKRRKK | 20 | 6 |
| Short-chain peptide 7 | 45 | KKRKEQQNAFYEILHKRRKK | 20 | 7 |
| Short-chain peptide 8 | 46 | KKRKEQQKKFYKKLHK | 16 | 9 |

[*1]: "Ac-" represents N-terminal acetylation.

In Table 3, the number of immobilizing functional groups is the sum of amino groups in the side chains of lysine residues (ε-amino groups) and the N-terminal amino groups (α-amino groups).

Furthermore, the percentage contents of the secondary structures of short-chain peptides 1 to 8 described in Table 3 in a HEPES (4-(2-hydroxyethyl)-1-piperazine ethanesulfonic acid) buffer solution and in methanol (MeOH) are presented in Table 4.

TABLE 4

| Short-chain peptide name | Percentage content of secondary structure | |
|---|---|---|
| | In HEPES | In MeOH |
| Short-chain peptide 1 | 43% | 100% |
| Short-chain peptide 2 | 30% | 84% |
| Short-chain peptide 3 | 33% | 100% |
| Short-chain peptide 4 | 32% | 100% |
| Short-chain peptide 5 | 36% | 92% |
| Short-chain peptide 6 | 35% | 100% |
| Short-chain peptide 7 | 35% | 100% |
| Short-chain peptide 8 | 16% | 88% |

The percentage contents of the secondary structures of short-chain peptides 1 to 8 in a HEPES buffer solution or in methanol (MeOH) were obtained by measuring the CD (circular dichroism) spectra of the various short-chain peptides in a HEPES solution or in a methanol solution using a circular dichroism dispersion meter (J-820, manufactured by JASCO Corp.), and analyzing the secondary structures using a protein secondary structure analysis program (JWSSE-480, manufactured by JASCO Corp.) based on the CD spectra thus obtained. In Table 4, short-chain peptides 1 to 8 are the short-chain peptides 1 to 8 described in Table 3, respectively. Furthermore, the term "In HEPES" represents the percentage content of the secondary structure in a HEPES buffer solution (10 mM HEPES (4-(2-hydroxyethyl)-1-piperazine ethanesulfonic acid)-HCl (hydrochloric acid), 150 mM NaCl (sodium chloride), pH 7.4, 25° C.), and the term "In MeOH" represents the percentage content of the secondary structure in methanol (purity 99.5% by mass).

In all of the short-chain peptides 1 to 8, the percentage content of the secondary structure in methanol (MeOH) was from 2 times to 4 times the percentage content of the secondary structure in HEPES, and since the percentage contents were 1.5 times or more, the short-chain peptides were short-chain peptides that have their secondary structures induced in an alcohol solvent.

Example 1

(1) Immobilization of Spacer

50 µL of a DMSO (dimethyl sulfoxide; manufactured by Wako Pure Chemical Industries, Ltd.) solution including 0.47 M EDC (1-ethyl-3-(3-dimethylaminopropyl)carbodiimide, manufactured by Wako Pure Chemical Industries, Ltd.) and 0.35 M NHS (N-hydroxysuccinimide; manufactured by Wako Pure Chemical Industries, Ltd.) was added to a commercially available CM5 sensor chip (carboxymethyl dextran-introduced type, manufactured by GE Healthcare, Inc.), and the sensor chip was activated for one hour at room temperature.

After the sensor chip was washed with DMSO, an amino group-terminated polyacrylic acid (mass average molecular weight (Mw): 3120) (hereinafter, may be referred to as "polyacrylic acid 1") was dissolved in a DMSO (dimethyl sulfoxide)/DBU (1,8-diazabicyclo[5.4.0]undec-7-ene) (85:15 vol %) solution to prepare a 50 mM solution, and 20 µL of the solution was added to the sensor chip. The solution and the sensor chip were allowed to react for 2 hours at room temperature.

Subsequently, the sensor chip was washed with DMSO, and then was subjected to a blocking treatment using an ethanolamine solution. Thus, a spacer-immobilized carrier (hereinafter, may be referred to as "carrier A") was obtained.

(2) Immobilization of Ligand

The carrier A obtained in section "(1) Immobilization of spacer" was mounted in a surface plasmon resonance apparatus (BIACORE 3000, manufactured by GE Healthcare, Inc.), a HEPES buffer solution for SPR (Surface Plasmon Resonance) (10 mM HEPES (4-(2-hydroxyethyl)-1-piperazine ethanesulfonic acid)-HCl (hydrochloric acid), 150 mM NaCl (sodium chloride), pH 7.4) was stabilized at a flow rate of 10 µL/min, and 70 µL of a mixed aqueous solution of 0.2 M EDC (1-ethyl-3-(3-dimethylaminopropyl)carbodiimide) and 0.04 M NHS (N-hydroxysuccinimide) was added to the buffer solution. Subsequently, 10 µL of a sample solution of Short-chain peptide 1 diluted to 4 µM with methanol (corresponding to the immobilization solvent) was supplied to a carrier sample, and then the carrier sample was subjected to a blocking treatment using an ethanolamine solution. The carrier sample was washed with an aqueous solution of sodium hydroxide, and thereby immobilization was performed. Short-chain peptide 1 was immobilized on the carrier A in another flow channel by the same procedure, using a sample solution of Short-chain peptide 1 that had been diluted to 4 µM with a HEPES buffer solution. The immobilized carrier thus obtained will be hereinafter referred to as "immobilized carrier A".

(3) Evaluation of Antibody-Binding Property Improvement Ratio 10 to 3,000 nM human IgG antibody was added for 10 minutes to the immobilized carrier A produced in section "(2) Immobilization of ligand", and dissociation at 25° C. in a HEPES buffer solution was measured. The binding rate Kon [nM/s] and the dissociation rate Koff [1/s] of the antibody were calculated from a binding reaction curve. Furthermore, the dissociation constants Kd [nM] for the binding reaction between the Short-chain peptide 1 and human IgG antibody in the case in which the carrier was immobilized using methanol and a HEPES buffer solution, respectively, were calculated. The dissociation constant Kd [nM] obtained at the time of immobilizing the carrier in methanol, with respect to the dissociation constant Kd [nM] obtained at the time of immobilizing the carrier in the HEPES buffer solution, was designated as the antibody-binding property improvement ratio. This ratio was evaluated according to the following evaluation criteria for the antibody-binding property improvement ratio, and the results are presented in the column of "Antibody-binding property improvement ratio" in Table 5.

| (Evaluation criteria for antibody-binding property improvement ratio) | |
| --- | --- |
| Improvement ratio of dissociation constant (Kd) is more than 10 times | A |
| Improvement ratio of dissociation constant (Kd) is more than 3 times and 10 times or less | B |
| Improvement ratio of dissociation constant (Kd) is more than 2 times and 3 times or less | C |
| Improvement ratio of dissociation constant (Kd) is more than 1 time and 2 times or less | D |
| Improvement ratio of dissociation constant (Kd) is 1 time or less | E |

Evaluation grades A, B, and C indicate that the effect of improvement by the present immobilization is sufficient, and evaluation grades D and E indicate that a sufficient improvement effect is not observed. By using a ligand-immobilized state that shows a sufficient improvement effect, the carrier can specifically bind to an antibody, and an antibody can be purified more efficiently. Thus, the cost for purification of an antibody can be further reduced.

Fitting was performed using a fitting software program (BIAEVALUATION 4.1, manufactured by GE Healthcare, Inc.), and the CD (circular dichroism) spectra of the respective peptides in various solutions were measured. Thus, the percentage contents of secondary structures were calculated. The percentage contents of secondary structures thus calculated are presented in the column for "Percentage content of secondary structure" in Table 5.

Example 2

(1) An immobilized carrier B was obtained in the same manner as in Example 1, except that short-chain peptide 2 was used instead of short-chain peptide 1.

(2) The antibody-binding property improvement ratio was evaluated in the same manner as in Example 1 using the immobilized carrier B, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 3

(1) An immobilized carrier C was obtained in the same manner as in Example 1, except that short-chain peptide 3 was used instead of short-chain peptide 1, and a polyacrylic acid 2 (amino group-terminated poly(acrylic acid), Mw: 1,350).DMSO/DBU (1,8-diazabicyclo[5.4.0]undec-7-ene) (94:6 vol %) solution was used as the spacer instead of the polyacrylic acid 1 (amino group-terminated poly(acrylic acid), Mw: 3,120).DMSO/DBU (1,8-diazabicyclo[5.4.0]undec-7-ene) (85:15 vol %) solution.

(2) The antibody-binding property improvement ratio was evaluated in the same manner as in Example 1 using the immobilized carrier C, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 4

(1) An immobilized carrier D was obtained in the same manner as in Example 1, except that short-chain peptide 3 was used instead of short-chain peptide 1.

(2) The antibody-binding property improvement ratio was evaluated in the same manner as in Example 1 using the immobilized carrier D, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 5

(1) An immobilized carrier E was obtained in the same manner as in Example 1, except that short-chain peptide 3 was used instead of short-chain peptide 1, and a polyacrylic acid 3 (amino group-terminated poly(acrylic acid), Mw: 8,400).DMSO/DBU (1,8-diazabicyclo[5.4.0]undec-7-ene) (68:32 vol %) solution was used as the spacer instead of the polyacrylic acid 1 (amino group-terminated poly(acrylic acid), Mw: 3,120).DMSO/DBU (1,8-diazabicyclo[5.4.0]undec-7-ene) (85:15 vol %) solution.

(2) The antibody-binding property improvement ratio was evaluated in the same manner as in Example 1 using the immobilized carrier E, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 6

(1) An immobilized carrier F was obtained in the same manner as in Example 1, except that short-chain peptide 3 was used instead of short-chain peptide 1, and isopropyl alcohol (IPA) was used as the immobilization solvent for immobilizing the ligand, instead of methanol (MeOH).

(2) The antibody-binding property improvement ratio was evaluated in the same manner as in Example 1 using the immobilized carrier F, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 7

(1) An immobilized carrier G was obtained in the same manner as in Example 1, except that short-chain peptide 3 was used instead of short-chain peptide 1, and ethanol (EtOH) was used as the immobilization solvent for immobilizing the ligand, instead of methanol (MeOH).

(2) The antibody-binding property improvement ratio was evaluated in the same manner as in Example 1 using the immobilized carrier and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 8

(1) An immobilized carrier H was obtained in the same manner as in Example 1, except that short-chain peptide 4 was used instead of short-chain peptide 1.

(2) The antibody-binding property improvement ratio was evaluated in the same manner as in Example 1 using the immobilized carrier H, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 9

(1) An immobilized carrier I was obtained in the same manner as in Example 1, except that short-chain peptide 5 was used instead of short-chain peptide 1.

(2) The antibody-binding property improvement ratio was evaluated in the same manner as in Example 1 using the immobilized carrier I, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 10

(1) An immobilized carrier J was obtained in the same manner as in Example 1, except that short-chain peptide 6 was used instead of short-chain peptide 1.

(2) The antibody-binding property improvement ratio was evaluated in the same manner as in Example 1 using the immobilized carrier J, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 11

(1) An immobilized carrier K was obtained in the same manner as in Example 1, except that short-chain peptide 7 was used instead of short-chain peptide 1.

(2) The antibody-binding property improvement ratio was evaluated in the same manner as in Example 1 using the immobilized carrier K, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Example 12

(1) An immobilized carrier L was obtained in the same manner as in Example 1, except that short-chain peptide 8 was used instead of short-chain peptide 1.

(2) The antibody-binding property improvement ratio was evaluated in the same manner as in Example 1 using the immobilized carrier L, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Comparative Example 1

(1) An immobilized carrier M was obtained in the same manner as in Example 1, except that HEPES (4-(2-hydroxyethyl)-1-piperazine ethanesulfonic acid) was used as the immobilization solvent for immobilizing the ligand, instead of methanol (MeOH). Furthermore, an immobilized carrier M2 was obtained in the same manner as in Example 1, except that a CM5 sensor chip was used without performing the spacer immobilization operation, and HEPES was used instead of methanol.

(2) The antibody-binding property improvement ratio of the immobilized carrier M with respect to the immobilized carrier M2 was evaluated using the immobilized carrier M and the immobilized carrier M2, and the percentage content of secondary structure was calculated in the same manner as in Example 1 using the immobilized carrier M. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Comparative Example 2

(1) An immobilized carrier N was obtained in the same manner as in Example 1, except that a CM5 sensor chip was used without performing the spacer immobilization operation.

(2) The antibody-binding property improvement ratio was evaluated in the same manner as in Example 1 using the immobilized carrier N, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

Comparative Example 3

(1) An immobilized carrier O was obtained in the same manner as in Example 1, except that short-chain peptide 3 was used instead of short-chain peptide 1, and a CM5 sensor chip was used without performing the spacer immobilization operation.

(2) The antibody-binding property improvement ratio was evaluated in the same manner as in Example 1 using the immobilized carrier O, and the percentage content of secondary structure was calculated. The evaluation results for the antibody-binding property improvement ratio are presented in the column for "Antibody-binding property improvement ratio" in Table 5, and the percentage content of secondary structure thus calculated is presented in the column for "Percentage content of secondary structure" in Table 5.

In Table 5, Short-chain peptides 1 to 8 represent the short-chain peptides 1 to 8 described in Table 3, respectively.

In Table 5, in the column for the immobilization solvent, MeOH represents methanol; EtOH represents ethanol; IPA represents isopropyl alcohol; and HEPES represents 4-(2-hydroxyethyl)-1-piperazine ethanesulfonic acid.

In Table 5, Polyacrylic acid 1 represents an amino group-terminated poly(acrylic acid) (Mw: 3,120); Polyacrylic acid 2 represents an amino group-terminated poly(acrylic acid) (Mw: 1,350); and Polyacrylic acid 3 represents an amino group-terminated poly(acrylic acid) (Mw: 8,400).

The immobilized carriers of Examples 1 to 12 had superior evaluation results for the antibody-binding property improvement ratio, and had excellent antibody-binding property. This is speculated to be because the short-chain peptides could be immobilized on the carrier while maintaining the secondary structure induced in an alcohol solvent.

On the other hand, the immobilized carriers of Comparative Examples 1 to 3 had low evaluation results for the antibody-binding property improvement ratio, and had inferior antibody-binding property compared to Examples 1 to 12. This is speculated to be because the short-chain peptides could not be immobilized on the carrier while maintaining the secondary structure induced in an alcohol solvent.

SEQUENCE LISTING

International application W-5661 PCT based on International Patent Cooperation Treaty method for producing a short-chain peptide-immobilized carrier JP 16060907 20160401 - - - 000600760516006694 31 Normal 20160401092425201603151608386370 AP 1AP101_W-_5.app

TABLE 5

| | | Ligand | Immobilization solvent | Percentage content of secondary structure | Immobilized carrier | Spacer | Antibody-binding property improvement ratio |
|---|---|---|---|---|---|---|---|
| Example | 1 | Short-chain peptide 1 | MeOH | 100% | A | Polyacrylic acid 1 | B |
| | 2 | Short-chain peptide 2 | MeOH | 84% | B | Polyacrylic acid 1 | A |
| | 3 | Short-chain peptide 3 | MeOH | 100% | C | Polyacrylic acid 2 | A |
| | 4 | Short-chain peptide 3 | MeOH | 100% | D | Polyacrylic acid 1 | A |
| | 5 | Short-chain peptide 3 | MeOH | 100% | E | Polyacrylic acid 3 | A |
| | 6 | Short-chain peptide 3 | IPA | 100% | F | Polyacrylic acid 1 | A |
| | 7 | Short-chain peptide 3 | EtOH | 100% | G | Polyacrylic acid 1 | A |
| | 8 | Short-chain peptide 4 | MeOH | 100% | H | Polyacrylic acid 1 | A |
| | 9 | Short-chain peptide 5 | MeOH | 92% | I | Polyacrylic acid 1 | A |
| | 10 | Short-chain peptide 6 | MeOH | 100% | J | Polyacrylic acid 1 | A |
| | 11 | Short-chain peptide 7 | MeOH | 100% | K | Polyacrylic acid 1 | A |
| | 12 | Short-chain peptide 8 | MeOH | 88% | L | Polyacrylic acid 1 | A |
| Comparative Example | 1 | Short-chain peptide 1 | HEPES | 43% | M | Polyacrylic acid 1 | D |
| | 2 | Short-chain peptide 1 | MeOH | 100% | N | None | E |
| | 3 | Short-chain peptide 3 | MeOH | 100% | O | None | E |

What is claimed is:

1. A method for producing a short-chain peptide-immobilized carrier, the method comprising:
a step of preparing an alcohol solution containing an alcohol solvent, and a short-chain peptide having a plurality of immobilizing functional groups and having 50 residues or fewer; and
a step of bringing a carrier coupled with a spacer having a reactive group that reacts with the immobilizing functional group, into contact with the alcohol solution, and thereby immobilizing the short-chain peptide to the spacer, the spacer being polyacrylic acid,
wherein the short-chain peptide has a structure composed of an antibody-binding domain and a spacer-binding domain, or a structure further containing a linker connecting between the domains,
the short-chain peptide has one of the amino acid sequences set forth in SEQ ID) NO:39 to SEQ ID NO:46,
the alcohol is at least one selected from the group consisting of methanol, ethanol, and isopropyl alcohol, and
the carrier is carboxymethyl dextran.

2. The method for producing a short-chain peptide-immobilized carrier according to claim 1, wherein the short-chain peptide has 34 residues or fewer.

3. The method for producing a short-chain peptide-immobilized carrier according to claim 1, wherein the short-chain peptide and the spacer are immobilized by covalent bonding.

4. The method for producing a short-chain peptide-immobilized carrier according to claim 2, wherein the short-chain peptide and the spacer are immobilized by covalent bonding.

5. The method for producing a short-chain peptide-immobilized carrier according to claim 1, wherein the spacer has a molecular weight of 10,000 or less.

6. The method for producing a short-chain peptide-immobilized carrier according to claim 2, wherein the spacer has a molecular weight of 10,000 or less.

7. The method for producing a short-chain peptide-immobilized carrier according to claim 1, wherein the immobilizing functional group is at least one selected from the group consisting of a thiol group and an amino group.

8. The method for producing a short-chain peptide-immobilized carrier according to claim 2, wherein the immobilizing functional group is at least one selected from the group consisting of a thiol group and an amino group.

9. The method for producing a short-chain peptide-immobilized carrier according to claim 3, wherein the immobilizing functional group is at least one selected from the group consisting of a thiol group and an amino group.

10. The method for producing a short-chain peptide-immobilized carrier according to claim 1, wherein the immobilizing functional group is positioned at at least one terminal of the short-chain peptide.

11. The method for producing a short-chain peptide-immobilized carrier according to claim 2, wherein the immobilizing functional group is positioned at at least one terminal of the short-chain peptide.

12. The method for producing a short-chain peptide-immobilized carrier according to claim 3, wherein the immobilizing functional group is positioned at at least one terminal of the short-chain peptide.

13. The method for producing a short-chain peptide-immobilized carrier according to claim 5, wherein the immobilizing functional group is positioned at at least one terminal of the short-chain peptide.

14. The method for producing a short-chain peptide-immobilized carrier according to claim 1, wherein the short-chain peptide has a plurality of amino acid residues each having the immobilizing functional group, and the short-chain peptide has a partial structure containing at least one amino acid residue that does not have an immobilizing functional group, between the amino acid residues having an immobilizing functional group.

15. The method for producing a short-chain peptide-immobilized carrier according to claim 2, wherein the short-chain peptide has a plurality of amino acid residues each having the immobilizing functional group, and the short-chain peptide has a partial structure containing at least one amino acid residue that does not have an immobilizing functional group, between the amino acid residues having an immobilizing functional group.

16. The method for producing a short-chain peptide-immobilized carrier according to claim 3, wherein the short-chain peptide has a plurality of amino acid residues each having the immobilizing functional group, and the short-chain peptide has a partial structure containing at least one amino acid residue that does not have an immobilizing functional group, between the amino acid residues having an immobilizing functional group.

17. The method for producing a short-chain peptide-immobilized carrier according to claim 1, wherein the immobilizing functional group is at least one selected from the group consisting of a thiol group, an amino group, a carboxyl group, a diazo group, a chloroacetyl group, an olefin group, a glycidyl group, a carbene group, a hydroxyl group, and a formyl group.

* * * * *

SEQUENCE LISTING

<160> NUMBER OF SEQ ID NOS: 51

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Glu Gln Gln Asn Ala Phe Tyr
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Glu Gln Gln Asn Ala Phe Tyr Glu Ile Leu His
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Glu Gln Gln Asn Ala Phe Tyr Glu Ile Leu His Leu
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Glu Gly Gln Asn Ala Phe Tyr
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Glu Gly Gln Asn Ala Phe Tyr Glu Ile Leu His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Glu Gly Gln Asn Ala Phe Tyr Glu Ile Leu His Leu
1               5                   10

```
<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Glu Gln Asn Ala Phe Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Glu Gln Asn Ala Phe Tyr Glu Ile Leu His
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Glu Gln Asn Ala Phe Tyr Glu Ile Leu His Leu
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Glu Gln Gln Ser Ala Phe Tyr
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Glu Gln Gln Ser Ala Phe Tyr Glu Ile Leu His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide

<400> SEQUENCE: 12

Glu Gln Gln Ser Ala Phe Tyr Glu Ile Leu His Leu
1               5                   10
```

```
<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Asp Gln Gln Ser Ala Phe Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Asp Gln Gln Ser Ala Phe Tyr Glu Ile Leu His
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide

<400> SEQUENCE: 15

Asp Gln Gln Ser Ala Phe Tyr Glu Ile Leu His Leu
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Glu Ala Gln Gln Ser Ala Phe Tyr
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide

<400> SEQUENCE: 17

Glu Ala Gln Gln Ser Ala Phe Tyr Glu Ile Leu His
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

Glu Ala Gln Gln Ser Ala Phe Tyr Glu Ile Leu His Leu
1               5                   10
```

```
<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Glu Gln Ser Ala Phe Tyr
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Glu Gln Ser Ala Phe Tyr Glu Ile Leu His
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Glu Gln Ser Ala Phe Tyr Glu Ile Leu His Leu
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Glu Ala Gln Gln Asn Ala Phe Tyr
1               5

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide

<400> SEQUENCE: 23

Glu Ala Gln Gln Asn Ala Phe Tyr Glu Ile Leu His
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide

<400> SEQUENCE: 24

Glu Ala Gln Gln Asn Ala Phe Tyr Glu Ile Leu His Leu
1               5                   10
```

```
<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Asp Ala Gln Gln Ser Ala Phe Tyr
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic peptide

<400> SEQUENCE: 26

Asp Ala Gln Gln Ser Ala Phe Tyr Glu Ile Leu His
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic peptide

<400> SEQUENCE: 27

Asp Ala Gln Gln Ser Ala Phe Tyr Glu Ile Leu His Leu
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Asp Gln Ser Ala Phe Tyr
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide

<400> SEQUENCE: 29

Asp Gln Ser Ala Phe Tyr Glu Ile Leu His
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide

<400> SEQUENCE: 30

Asp Gln Ser Ala Phe Tyr Glu Ile Leu His Leu
1               5                   10
```

```
<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Glu Gln Gln Lys Lys Phe Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Glu Gln Gln Asn Lys Phe Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Glu Gln Gln Ser Lys Phe Tyr
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Glu Gln Gln Lys Ala Phe Tyr
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide

<400> SEQUENCE: 35

Glu Ala Gln Gln Lys Lys Phe Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Glu Ala Gln Gln Asn Lys Phe Tyr
1               5
```

<210> SEQ ID NO 37
<211> LENGTH: 8
<212> TYPE: PRT
<213> ORGANISM: Artificial Sequence
<220> FEATURE:
<223> OTHER INFORMATION: Synthetic peptide

<400> SEQUENCE: 37

Glu Ala Gln Gln Ser Lys Phe Tyr
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide

<400> SEQUENCE: 38

Glu Ala Gln Gln Lys Ala Phe Tyr
1               5

<210> SEQ ID NO 39
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: SIMILAR
<222> LOCATION: (6)..(12)
<223> OTHER INFORMATION: SEQ ID No.1: EQQNAFY
<220> FEATURE:
<221> NAME/KEY: SIMILAR
<222> LOCATION: (6)..(16)
<223> OTHER INFORMATION: SEQ ID No.2: EQQNAFYEILH
<220> FEATURE:
<221> NAME/KEY: SIMILAR
<222> LOCATION: (6)..(17)
<223> OTHER INFORMATION: SEQ ID No.3: EQQNAFYEILHL

<400> SEQUENCE: 39

Lys Lys Lys Lys Lys Glu Gln Gln Asn Ala Phe Tyr Glu Ile Leu His
1               5                   10                  15

Leu Pro Asn Leu Thr Glu Glu Gln Arg Asn Ala Phe Ile Gln Ser Leu
            20                  25                  30

Arg Asp

<210> SEQ ID NO 40
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: SIMILAR
<222> LOCATION: (6)..(12)
<223> OTHER INFORMATION: SEQ ID No.1: EQQNAFY
<220> FEATURE:
<221> NAME/KEY: SIMILAR
<222> LOCATION: (6)..(16)
<223> OTHER INFORMATION: SEQ ID No.2: EQQNAFYEILH

<400> SEQUENCE: 40

Lys Lys Lys Lys Lys Glu Gln Gln Asn Ala Phe Tyr Glu Ile Leu His
1               5                   10                  15

```
<210> SEQ ID NO 41
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: SIMILAR
<222> LOCATION: (4)..(14)
<223> OTHER INFORMATION: SEQ ID No.2: EQQNAFYEILH
<220> FEATURE:
<221> NAME/KEY: SIMILAR
<222> LOCATION: (4)..(10)
<223> OTHER INFORMATION: SEQ ID No.1: EQQNAFY

<400> SEQUENCE: 41

Lys Lys Lys Glu Gln Gln Asn Ala Phe Tyr Glu Ile Leu His Lys Lys
1               5                   10                  15
Lys

<210> SEQ ID NO 42
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: SIMILAR
<222> LOCATION: (5)..(11)
<223> OTHER INFORMATION: SEQ ID No.1: EQQNAFY
<220> FEATURE:
<221> NAME/KEY: SIMILAR
<222> LOCATION: (5)..(15)
<223> OTHER INFORMATION: SEQ ID No.2: EQQNAFYEILH

<400> SEQUENCE: 42

Lys Lys Lys Lys Glu Gln Gln Asn Ala Phe Tyr Glu Ile Leu His Lys
1               5                   10                  15
Lys Lys Lys

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 43

Lys Ala Ala Lys Glu Gln Gln Lys Ala Phe Tyr Lys Ile Leu His
1               5                   10                  15

<210> SEQ ID NO 44
<211> LENGTH: 20
<212> TYPE: PRT
<213> ORGANISM: Artificial Sequence
<220> FEATURE:
<223> OTHER INFORMATION: Synthetic peptide

<400> SEQUENCE: 44

Lys Lys Arg Arg Glu Gln Gln Asn Ala Phe Tyr Glu Ile Leu His Lys
1               5                   10                  15
Arg Arg Lys Lys
            20
```

```
<210> SEQ ID NO 45
<211> LENGTH: 20
<212> TYPE: PRT
<213> ORGANISM: Artificial Sequence
<220> FEATURE:
<223> OTHER INFORMATION: Synthetic peptide

<400> SEQUENCE: 45

Lys Lys Arg Lys Glu Gln Gln Asn Ala Phe Tyr Glu Ile Leu His Lys
1               5                   10                  15

Arg Arg Lys Lys
            20

<210> SEQ ID NO 46
<211> LENGTH: 16
<212> TYPE: PRT
<213> ORGANISM: Artificial Sequence
<220> FEATURE:
<223> OTHER INFORMATION: Synthetic peptide

<400> SEQUENCE: 46

Lys Lys Arg Lys Glu Gln Gln Lys Lys Phe Tyr Lys Lys Leu His Lys
1               5                   10                  15

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Lys Lys Lys Glu Gln Gln Asn Ala Phe Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

Glu Gln Gln Asn Ala Phe Tyr Lys Lys Lys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic peptide

<400> SEQUENCE: 49

Lys Lys Lys Glu Gln Gln Asn Ala Phe Tyr Lys Lys Lys
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Synthetic peptide
```

```
<400> SEQUENCE: 50

Lys Glu Gln Gln Asn Ala Phe Tyr Lys Glu Gln Gln Asn Ala Phe Tyr
1               5                   10                  15

Lys

<210> SEQ ID NO 51
<211> LENGTH: 8
<212> TYPE: PRT
<213> ORGANISM: Artificial Sequence
<220> FEATURE:
<223> OTHER INFORMATION: Synthetic peptide

<400> SEQUENCE: 51

Lys Glu Gln Gln Ser Ala Phe Tyr
1               5
```